United States Patent [19]

Giger

[11] Patent Number: 4,602,032
[45] Date of Patent: Jul. 22, 1986

[54] DIBENZ[CD,F]INDOLE DERIVATIVES, THEIR PREPARATION AND PHARMACEUTICAL COMPOSITIONS CONTAINING THEM

[75] Inventor: Rudolf K. A. Giger, Riehen, Switzerland

[73] Assignee: Sandoz Ltd., Basel, Switzerland

[21] Appl. No.: 683,378

[22] Filed: Dec. 19, 1984

Related U.S. Application Data

[63] Continuation of Ser. No. 482,214, Apr. 5, 1983, abandoned.

[30] Foreign Application Priority Data

Apr. 13, 1982 [CH] Switzerland .......................... 2231/82

[51] Int. Cl.[4] ..................... A61K 31/40; C07D 209/56

[52] U.S. Cl. ...................................... 514/410; 548/425; 564/222; 564/308

[58] Field of Search ................. 548/420, 425; 514/410

[56] References Cited

FOREIGN PATENT DOCUMENTS 2024818A 1/1980 United Kingdom .
2078225A 1/1982 United Kingdom ................ 548/420

Primary Examiner—Joseph Paul Brust
Attorney, Agent, or Firm—Gerald D. Sharkin; Robert S. Honor; Thomas O. McGovern

[57] ABSTRACT

A 2-alkyl-9,10-dioxy-4,5,5a,6-tetrahydro-dibenz[cd,f]indole or an acid addition salt thereof is a useful anti-parkinson agent.

8 Claims, No Drawings

DIBENZ[CD,F]INDOLE DERIVATIVES, THEIR PREPARATION AND PHARMACEUTICAL COMPOSITIONS CONTAINING THEM

This is a continuation of application Ser. No. 482,214, filed Apr. 5, 1983 now abandoned.

The present invention relates to dibenz[cd,f]indole derivatives, their preparation and pharmaceutical compositions containing them.

Belgian Pat. No. 877 169 describes a class of 4,5,5a,6-tetrahydro-dibenz[cd,f]indole derivatives having at least one oxy sbustituent in one or both of the fused benzene rings and having stimulant activity on central dopaminergic receptors. All the compounds specifically exemplified contain only oxy substituents in one fused benzene ring, i.e. in positions 9 and 10, and no substituent in the other fused benzene ring. It has now been surprisingly found that a group of 4,5,5a,6-tetrahydro-dibenz[cd,f]indole derivatives substituted by alkyl in the 2 position and by oxy substituents in the 9 and 10 positions the dibenz[cd,f]indole nucleus, which are nowhere specifically described or suggested in this patent, exhibit particularly interesting pharmacological properties, e.g. a specific central dopaminergic activity and are well tolerated, e.g. in rats.

In accordance with the invention, there are thus provided 2-alkyl-9,10-dioxy-4,5,5a,6-tetrahydro-dibenz[cd,f]indoles and acid addition salts thereof hereinafter referred to as "the compounds of the invention".

The oxy substituent may be for example a hydroxy group or a group which is hydrolysable under physiological conditions to an hydroxy group, e.g. an acyloxy group. Alternatively it may be an ether group.

The compounds of the invention may be if desired substituted in the other positions of the dibenz[cd,f]indole nucleus, preferably in the 5 position and conveniently in the 4 position.

More particularly the present invention provides a (4R*,5aS*) compound of formula I

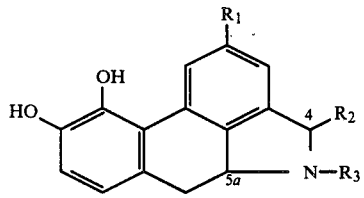

wherein
$R_1$ is $(C_{1-4})$alkyl,
$R_2$ is hydrogen, $(C_{1-10})$alkyl, $(C_{3-7})$cycloalkyl or $(C_{3-7})$cycloalkyl$(C_{1-4})$alkyl, and
$R_3$ is $(C_{1-5})$alkyl, or a physiologically hydrolysable and acceptable ester thereof, and acid addition salts of the compound or ester.

The term (4R*,5aS*) according to the usual convention indicates that the compound may be in the form of the racemate or optically isomer wherein the hydrogen atoms in positions 4 and 5a of the dibenz[cd,f]indole nucleus are cis to each other. The optical isomers having the absolute configuration 4S,5aR are preferred.

Any alkyl radicals preferably are straight chain radicals.

$R_1$ is preferably methyl.

When $R_2$ is an alkyl radical, this contains preferably 1 to 4 carbon atoms, and is especially n-propyl.

Conveniently, $R_3$ has preferably 2 or 3 carbon atoms, and is especially ethyl.

One group of compounds in accordance with the present invention comprises the compounds of formula I as defined above, wherein $R_2$ is $(C_{1-4})$alkyl and $R_3$ is $(C_{1-3})$alkyl as the racemate or (4S,5aR) optical isomer.

Physiologically hydrolysable and acceptable esters are esters which are hydrolysable under physiological conditions to yield the corresponding 9,10-dihydroxy-dibenz[cd,f]indole. Such esters include esters of monocarboxylic acids, in particular aliphatic or monoaromatic carboxylic acids of formula

R'COOH wherein R' is $(C_{1-17})$alkyl, $(C_{3-6})$cycloalkyl, phenyl, phenyl mono- or independently di-substituted by chlorine, fluorine, trifluoromethyl, $(C_{1-4})$alkyl or $(C_{1-4})$alkoxy, unsubstituted benzyl or benzyl mono-, or independently, di-substituted by chlorine, fluorine, $(C_{1-4})$alkyl or $(C_{1-4})$alkoxy.

The present invention provides also a process for the production of a compound of the invention or an acid addition salt thereof, which includes the steps of obtaining a 2-alkyl-9,10-dihydroxy-4,5,5a,6-tetrahydro-dibenz[cd,f]indole or an acid addition salt thereof, by splitting the ether groups in a corresponding 2-alkyl-4,5,5a,6-tetrahydro-dibenz[cd,f]indole having splittable ether groups in the 9 and 10 positions, or a precursor thereof, or interconverting an 2-alkyl-9,10-dioxy-4,5,5a,6-tetrahydro-dibenz[cd,f]indole or an acid addition salt thereof into another 2-alkyl-9,10-dioxy-4,5,5a,6-tetrahydro-dibenz[cd,f]indole or an acid addition salt thereof, and recovering the desired 2-alkyl-9,10-dioxy-4,5,5a,6-tetrahydro-dibenz[cd,f]indole as such or as an acid addition salt thereof, More particularly, the invention provides a process for the production of a (4R*,5aS*) compound of formula I

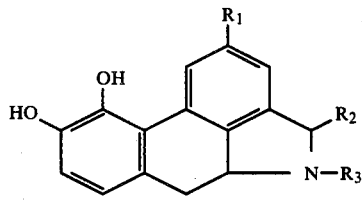

wherein
$R_1$ is $(C_{1-4})$alkyl,
$R_2$ is hydrogen, $(C_{1-10})$alkyl, $(C_{3-7})$cycloalkyl or $(C_{3-7})$cycloalkyl-$(C_{1-4})$alkyl, and
$R_3$ is $(C_{1-5})$alkyl, or a physiologically hydrolysable and acceptable ester thereof, or an acid addition salt of the compound or ester, which comprises (a) obtaining a (4R*,5aS*) compound of formula I or an acid addition salt thereof, by splitting the ether groups in a (4R*,5aS*) compound of formula II

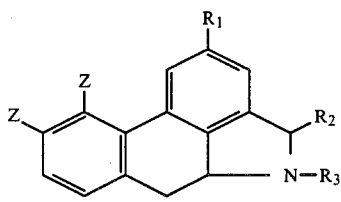 (II)

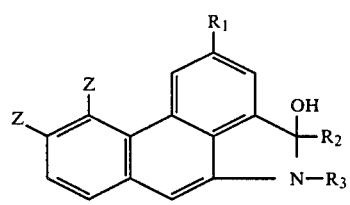 (III)

wherein R₁ to R₃ are as defined above, and the Z radicals are the same or different and are splittable ether groups, or a precursor thereof, or (b) obtaining a physiologically hydrolysable and acceptable ester of a (4R*,5aS*) compound of formula I or an acid addition salt thereof, by acylating a corresponding (4R*,5aS*) compound of formula I, and recovering the (4R*,5aS*) compound of formula I or a physiologically hydrolysable and acceptable ester as such or as an acid addition salt of the compound or ester.

The ether splitting process may be effected in conventional manner for splitting ether groups. For example the reaction may be carried out by treatment with a strong mineral acid, e.g. aqueous hydrobromic or hydroiodic acid. Suitable temperatures may be from 100° C. or higher, preferably from 100° C. to the boiling point of the reaction mixture, especially at about 130° C. The ether group Z is preferably (C₁₋₄)alkyl.

One compound of the invention may be converted into another compound of the invention in conventional manner. For example hydroxy groups in the 9, 10 positions may be acylated.

The acylation may be effected in conventional manner for the selective acylation of phenolic groups in the presence of an amine function. For example there may be used as acylating agent a functional derivative of an acid such as an acid chloride, acid bromide or an acid anhydride. Conveniently the reaction is carried out by reacting an acid chloride in the presence of trifluoroacetic acid at temperatures from 20° C. to the boiling point of the reaction mixture or in the presence of pyridine at temperatures from 0° C. to room temperature.

The 2-alkyl-4,5,5a,6-tetrahydro-dibenz[cd,f]indoles containing splittable ether groups in the 9 and 10 positions and acid addition—salts thereof, which are also compounds of the invention, may be produced by a process which includes the steps of reducing an appropriate 2-alkyl-4-hydroxy-4,5-dihydro-dibenz[cd,f]indole having splittable ether groups in the 9 and 10 positions, or a precursor thereof and recovering the desired 2-alkyl-4,5,5a,6-tetrahydro-dibenz(cd,f]indole having splittable ether groups on the 9 and 10 positions as such or as an acid addition salt thereof.

In particular the (4R*,5aS*) compound of formula II and acid addition salts thereof, may be prepared by reducing compounds of formula III wherein Z,R₁R₂ and R₃ are as defined above, or a precursor thereof, and recovering the desired (4R*,5aS*) compound of formula II as such or as an acid addition salt thereof.

The reduction may be effected in conventional manner, conveniently under acidic conditions suitable for the acidic reduction of enamines or imines, for example with zinc in an aqueous mineral acid, preferably hydrochloric acid, conveniently in the presence of a mercury (II) salt, for example mercury (II) chloride. The reaction may suitably be effected in the presence of for example ethanol. Suitable temperatures may be from 50° C. to the boiling point of the reaction mixture.

As used herein the term precursor refers to compounds which are capable of being converted into the starting materials in conventional manner, e.g. temporarily protected compounds.

The resulting compounds of the invention may be recovered from the reaction mixture and purified in known manner. The free base forms of the compounds of the invention, including the compounds of formula I and esters thereof and compounds of formula II, and including compounds specifically exemplified hereinafter, may be converted into acid addition salt forms in conventional manner and vice versa. Suitable acids for salt formation include, for example, hydrochloric acid.

Racemic compounds of the invention may be obtained from racemic starting materials. Optically active isomers may be obtained from optically active precursors or from the racemate. The enantiomers may be obtained from the racemate by known methods, for example by fractional crystallization of diastereoisomeric salts, e.g. their salts with (+)-di-O,O,-p-toluoyl-D-tartaric acid or (−)-di-O,O-p-toluoyl-L-tartaric acid. Racemic resolution into the optically active isomers may be effected at the final stage or at an earlier stage in the synthesis, e.g. before splitting of the ether groups, e.g. in a compound of formula II.

The starting materials 2-alkyl-4,5,5a,6-tetrahydro-dibenz[cd,f]indoles may be prepared according known methods, for example as described in the above, Belgian Pat. No. 877,169. For example starting materials of formula III may be prepared according the following reaction scheme:

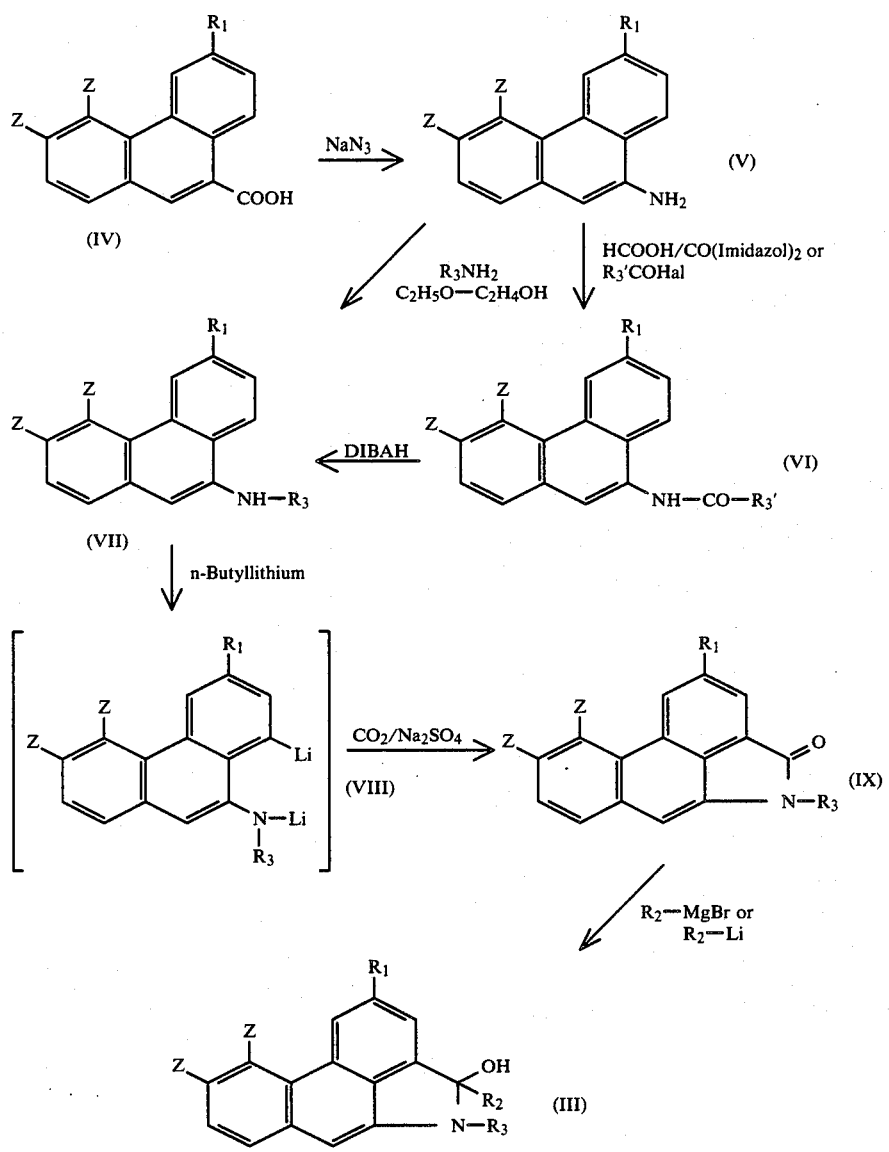

The compounds of formulae V to IX and III per se also form part of the present invention.

In the reaction scheme the radicals $R_1, R_2, R_3$ and Z are as defined above, $R_3'$ is hydrogen or methyl or ethyl and Hal is chlorine or bromine. The reactions may be carried out in conventional manner and the products of the above reactions may be isolated and purified in known manner.

In the above intermediates the ether groups Z are preferably methoxy.

Insofar the preparation or any particular starting material is not particularly described, this may be effected in conventional manner or in analogous manner to that described hereinafter for analogous compounds.

In the following Examples all temperatures are given in degrees Celsius and are uncorrected.

EXAMPLE 1

(±)(4R*,5aS*)-5-ethyl-4,5,5a,6-tetrahydro-9,10-dihydroxy-2-methyl-4-n-propyl-dibenz[cd,f]indole (a) 9-amino-3,4-dimethoxy-6-methyl-phenanthrene (compound of formula V)

A mixture of 400 ml (2.87M) of trifluoroacetic anhydride and 400 ml (5.22M) of trifluoroacetic acid is added at room temperature under a nitrogen atmosphere to 61.1 g (0.206M) of 3,4-dimethoxy-6-methyl-phenanthrene-9-carboxylic acid and the mixture is stirred for 10 minutes. After the mixture has been cooled to −5°, 16.08 g (0.247M) sodium azide are carefully added in solid form. The mixture is stirred for 2 hours at 0°, poured onto ice, extracted three times with methylene chloride and washed with a solution 1N of sodium hydroxide. The aqueous phases are extracted twice with methylene chloride 2-propanol 8:2. The organic phases are combined, dried and evaporated, to give white crystals. 86 g of the resultant mixed anhydride are warmed for 2 hours under reflux in 800 ml of a solution 2N of sodium hydroxide and 800 ml ethanol and the mixture is evaporated. The residue is washed with water/ice and extracted three times with methylene chloride. The organic phases are combined, dried and evaporated to give the title compound as an oil.

(b) 9-acetylamino-3,4-dimethoxy-6-methyl-phenanthrene (compound of formual VI)

105.7 ml (0.750M) of N-ethyl-N,N-diisopropyl-amine are added to a solution of 100.2 g (0.375M) of 9-amino-3,4-dimethoxy-6-methyl-phenanthrene in 1000 ml methylene chloride. To the resulting mixture is added dropwise over 30 minutes a solution of 34.5 ml (0.450M) of acetyl chloride in 250 ml methylene chloride. During the addition, the temperature of the reaction mixture is maintained at 20° by cooling with ice. The reaction mixture is stirred for 2 hours at room temperature and extracted with methylene chloride. The organic phases are washed with ice cooled 2N hydrochloric acid, water and 2N sodium bicarbonate, dried over sodium sulfate and evaporated, to give the title compound. M.pt. 190°–192° after crystallization from acetone/ether.

(c) 9-ethylamino-3,4-dimethoxy-6-methyl-phenanthrene (compound of formula VII)

1700 ml (2.05M) of a 20% solution of diisobutylaluminium hydride in toluene are added at room temperature over a period of 45 minutes to a suspension of 105.7 g (0.342M) of 9-acetylamino-3,4-dimethoxy-6-methyl-phenanthrene in 1500 ml anhydrous tetrahydrofuran. The mixture is then warmed with stirring under a nitrogen atmosphere for 2 hours at 80°. The reaction mixture is then cooled at 0° and under nitrogen atmosphere and a mixture of 2500 ml 2N hydrochloric acid/ice, cooled at −10°, is added by portions at such a rate that the gas evolution is maintained. The acid solution is made alkaline to pH 10 by addition at 0° of 3 liters 2N sodium hydroxide and the mixture is extracted three times with methylene chloride/2-propanol 7:3. The organic phases are combined, washed, dried and evaporated to give the title compound. M.pt. 100°–102° after crystallisation from acetone/ether.

(d) 5-ethyl-4,5-dihydro-9,10-dimethoxy-2-methyl-4-oxo-dibenz[cd,f]indole (compound of formula IX)

661.4 ml (1.084M) of a 15% solution of n-butyl-lithium in hexane are added at 0°, over a period of 20 minutes and under a nitrogen atmosphere, to a solution of 97 g (0.328M) of 9-ethylamino-3,4-dimethoxy-6-methyl-phenanthrene in 1000 ml anhydrous tetrahydrofuran; the reaction mixture becomes dark red. After stirring for 30 minutes at 0°, the mixture is transferred in portions with a teflon tube with nitrogen pressure at −50° onto a mixture of 500 g sodium sulfate and 500 g dry ice in 1500 ml tetrahydrofuran. After the temperature of the mixture has reached room temperature, the mixture is poured onto water/ice, extracted three times with methylene chloride. The combined organic phases are dried over sodium sulfate and evaporated to give the title compound. M.pt. 158°–160° (decomp.) after crystallisation from ether/petroleum ether.

(e) 5-ethyl-4,5-dihydro-4-hydroxy-9,10-dimethoxy-2-methyl-4-n-propyl-dibenz[cd,f]indole (compound of formula III)

A solution of 377 ml (4.1M) of n-propyl bromide in 4 liters tetrahydrofuran is added over a period of 90 minutes at reflux to 99.8 g (4.1M) of magnesium turnings and the mixture is stirred for one hour at reflux. To the resultant mixture is added dropwise over 30 minutes and under a nitrogen atmosphere a solution of 880 g (2.73M) of 5-ethyl-4,5-dihydro-9,10-dimethoxy-2-methyl-4-oxo-dibenz[cd,f]indole in 6 liters tetrahydrofuran. The reaction mixture is warmed for 2 hours at reflux and then extracted with methylene chloride. The organic phase is washed with a saturated solution of potassium bicarbonate and with water, dried over sodium sulfate and evaporated to give the title compound in the form of a red-brown oil [IR Spectrum ($CH_2Cl_2$): 3540 $cm^{-1}$ (OH)]. The crude product is directly used for the next step.

(f) (±)-(4R*,5aS*)-5-ethyl-4,5,5a,6-tetrahydro-9,10-dimethoxy-2-methyl-4-n-propyl-dibenz[cd,f]indole (compound of formula II)

A suspension of 100 g (0.273M) of 5-ethyl-4,5-dihydro-4-hydroxy-9,10-dimethoxy-2-methyl-4-n-propyl-dibenz[cd,f]indole in 2000 ml ethanol is added with stirring to a suspension of 322 g (4.928M) of zinc dust and 74.3 g (0.273M) of mercury(II) chloride in 2000 ml distilled water. The reaction mixture is refluxed, 450 ml of 18% hydrochloric acid are added dropwise over a period of 15 minutes and the mixture is refluxed overnight with stirring. The mixture is then cooled to room temperature, filtered and the zinc amalgam is washed with 500 ml methylene chloride. The filtrate is made alkaline with 1 liter of concentrated $NH_4OH$ and extracted three times with methylene chloride (700 ml each time). The combined organic phases are washed with water, dried and evaporated. The resultant oil is chromatographed on silica gel using methylene chloride with 2% methanol to give the title compound as an oil.

(g) (±)-(4R*,5aS*)-5-ethyl-4,5,5a,6-tetrahydro-9,10-dihydroxy-2-methyl-4-n-propyl-dibenz[cd,f]indole 100 g of (±)-(4R*,5aS*)-5-ethyl-4,5,5a,6-tetrahydro-9,10-dimethoxy-2-methyl-4-n-propyl-dibenz[cd,f]indole in 1 liter of a 47% aqueous solution of hydrobromic acid are warmed for 6 hours at reflux at a bath temperature of 150°. After evaporation of the mixture to dryness, the crystalline residue is stirred in acetone and filtered. The precipitate is washed with acetone then with ether and dried under high vacuum, to give the hydrobromide of the title compound. M.pt. 200° with decomposition. The hydrochloride melts at 185° with decomposition.

EXAMPLE 2

(−)-(4S,5aR)-5-ethyl-4,5,5a,6-tetrahydro-9,10-dihydroxy-2-methyl-4-n-propyl-dibenz[cd,f]indole (a) (−)-(4S,5aR)-5-ethyl-4,5,5a,6-tetrahydro-9,10-dimethoxy-2-methyl-4-n-propyl-dibenz[cd,f]indole 74.3 g (211 mM) of (±)-(4R*,5aS*)-5-ethyl-4,5,5a,6-tetrahydro-9,10-dimethoxy-2-methyl-4-n-propyl-dibenz[cd,f]indole are dissolved in 600 ml acetone and a solution of 81.67 g (211 mM) of (−)-di-O,O'-p-toluoyl-L-tartaric acid monohydrate in 300 ml acetone is added with stirring. The mixture is further stirred for one hour at room temperature, a total of 1 liter ether being added in portions during this period. The resultant precipitate is filtered off, washed with ethyl acetate until it remains light yellow, and dried.

114.7 g of the crystals obtained from the first crystallisation are dissolved in 1 liter $CH_2Cl_2$/methanol 7:3 at reflux and the solution is filtered and concentrated until a major part of the product crystallizes out. The mixture is stirred for about 15 minutes, the product is filtered off, washed with ethyl acetate until it remains colourless and dried.

48 g of the resulting product is recrystallised in the same manner by using 700 ml $CH_2Cl_2$/methanol 50:50 to give colourless crystals.

The resulting crystals are recrystallised in the same manner by using 1.2 liters acetone and 60 ml methanol. There is thus obtained (−)-(4S,5aR)-5-ethyl-4,5,5a,6-tetrahydro-9,10-dimethoxy-2-methyl-4-n-propyldibenz[cd,f]indole (−)-di-O.O-p-toluoyl-L-tartrate in form of colourless crystals which melt at 185°–198°; $[\alpha]_D^{20} = -150°$ (c=0.5 in methanol).

(b) (−)-(4S,5aR)-5-ethyl-4,5,5a,6-tetrahydro-9,10-dihydroxy-2-methyl-4-n-propyl-dibenz[cd,f]indole Proceeding as described in Example 1(g), (−)-(4S,5aR)-5-ethyl-4,5,5a,6-tetrahydro-9,10-dihydroxy-2-methyl-4-n-propyl-dibenz[cd,f]indole hydrobromide is obtained from the tartrate obtained above under (a). The corresponding hydrochloride melts at above 160° with decomposition; $[\alpha]_D^{20} = -94°$ (c=0.5 in methanol).

EXAMPLE 3

(4R*,5aS*)-4,5,5a,6-tetrahydro-9,10-dihydroxy-2-methyl-4,5-di-n-propyl-dibenz[cd,f]indole (±)(4R*,5aS*)-4,5,5a,6-tetrahydro-9,10-dimethoxy-2-methyl-4,5-di-n-propyl-dibenz[cd,f]indole, (oil), is obtained in analogous manner to Example 1a to (f). This compound is converted into the (−)-(4S,5aR) isomer form. Sintering of the hydrochloride at 210° and melting at 222°–224°; $[\alpha]_D^{20} = -127°$ (c=0.5 in methanol).

In analogous manner to Example 2 there is obtained (−)-(4S,5aR)-4,5,5a,6-tetrahydro-9,10-dihydroxy-2-methyl-4,5-di-n-propyl-dibenz[cd,f]indole hydrochloride. M.pt. above 145° with decomposition; $[\alpha]_D^{20} = -82.2°$ (c=0.45 in methanol).

It is also to be appreciated that 9-amino-3,4-dimethoxy-6-methyl-phenanthene may be converted directly into 9-ethylamino-3,4-dimethyloxy-6-methyl-phenanthrene by heating with ethylamine in 2-ethoxyethanol.

In analogous manner to that described in Example 1 and any conventional acylation techniques the following compounds of formula I may be obtained wherein $R_1$ is n-butyl, $R_2$ is H, n-nonyl, cycloheptyl or cyclopropylbutyl, $R_3$ is n-pentyl, and converted into esters of the following acids:

$nC_{17}H_{35}.CO.OH$

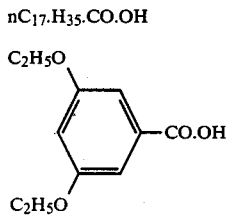

The compounds of the invention, in particular the compounds of formulae I and II, and their pharmaceutically acceptable acid addition salts thereof are useful because they possess pharmacological activity in animals and are therefore indicated for use as pharmaceuticals. In particular, the compounds are useful as central dopaminergic stimulant agents, as indicated by standard tests, for example according to the method of U. Ungerstedt et al [Acta Physiol.Scand.Supp.(1971), 387, Suppl.66–93], by induction of contralateral turning of notable duration in rats (whose substantia nigra has been lesioned by a microinjection of 6-hydroxy-dopamine one week previously) after i.p. and p.o. administration in an amount of 0.03 to about 10 mg/kg animal body weight. The activity is confirmed by induction of dose dependent sterotyped sniffing, licking and biting behaviour in the rat according to the following test, after i.p. administration in an amount of 1 to 30 mg/kg animal body weight.

Rats, 180–222 g, are placed in perspex cylinders of 30 cm diameter on a wire grid floor. After 30 minutes to allow acclimatisation to the cage, the rats are injected with the compond under investigation. The behaviour of the rats is observed for 2 minutes at 30 minutes intervals for 2 hours and then at 60 minute intervals for a total of up to 7 hours. The degree of stereotyped behaviour observed is assessed using a scoring system based on that described by Costall, Nayler and Olley [Europ. J.Pharmac.18, 83–94, (1972)].

The score and criteria are as follows:
1. Intermittent sniffing
2. Persistent sniffing, occasional licking
3. Licking, occasional biting
4. Intense and persistent biting.

The central dopaminergic activity is also confirmed by an inhibition of catalepsy induced by reserpine in mice on s.c. administration of about 0.01 mg to about 2 mg/kg of the compounds.

It is to be appreciated that the compounds of the invention having carboxylic acyloxy substituents may hydrolyse under physiological conditions to give the corresponding active compounds of the invention wherein the oxy substituents are hydroxy.

Moreover for the compounds of the invention especially the Example 2 compound, this central dopaminergic activity is specific as indicated in in vitro tests by no-affinity for clonidine receptors using the method described by A. Closse et al in "Psychopharmacology and Biochemistry of Neurotransmitter Receptors"., H. I. Yamanura, R. V. Olsen and E. Usdin, Edition, Elsevier North Holland Inc, Amsterdam, 1980, pages 463–465. This specifity is confirmed by a weak prolactin secretion inhibition activity and insignificant emesis in the dog at doses suitable for central dopaminergic activity.

The compounds are therefore useful as central dopaminergic stimulant agents, for example for treating Mobus Parkinson. For the above mentioned use the dosage will, of course, vary depending on the compound employed, mode of administration, and therapy desired. However, in general, satisfactory results are obtained when administered at a daily dosage of from 0.1 mg to about 30 mg per kg animal body weight.

This daily dosage is conveniently given in divided doses 2 to 4 times a day or in sustained release form. For the larger mammal, the total daily dosage is in the range from about 4 to about 30 mg, and dosage forms suitable for oral administration comprise from about 1 to about 15 mg of the compounds admixed with a solid or liquid pharmaceutical carrrier or diluent.

The compounds of the invention, in particular the compounds of formula I, are furthermore useful as antidepressant agents, as indicated by the inhibition of catalepsy induced by reserpine in mice on s.c. administration of about 0.01 mg to about 2 mg/kg of the compounds and by the inhibition of the catalepsy induced by tetrabenazine in rats on p.o. administration of about 5 to about 20 mg/kg of the compounds.

For this use the dosage will, of course, vary depending on the compound employed, mode of administration and therapy desired. However, in general, satisfactory results are obtained when administered at a daily dosage of from 0.001 to about 20 mg per kg animal body weight, conveniently given in divided doses 2 to 4 times a day, or in sustained release form. For the larger mammal, the total daily dosage is in the range from about 0.05 to about 2 mg, and dosage forms suitable for oral administration comprise from about 0.01 mg to about 1 mg of the compounds admixed with a solid or liquid pharmaceutical carrier or diluent.

The preferred indication is the anti-Parkinson indication. The preferred compound is the compound of Example 2.

The compounds may be administered in pharmaceutically acceptable acid addition salt form. These salt forms exhibit the same order or activity as the free base form.

The present invention also provides a pharmaceutical composition comprising a compound of the invention, e.g. a compound of formula I, a physiologically hydrolysable and acceptable ester thereof, or a compound of formula II, or a pharmaceutically acceptable acid addition salt thereof in association with a pharmaceutically acceptable diluent or carrier.

These compositions may be formulated in conventional manner so as to be for example a solution, a capsule or tablet.

The compounds of the invention may be used in analogous manner for known standards in the above indications, e.g. the known anti-parkinson agent, bromocriptine. The exact dose to be administered will depend on a number of factors, including activity in the above tests. For example, the preferred compound (−)-(4S,5aR)-5-ethyl-4,5,5a,6-tetrahydro-9,10-dihydroxy-2-methyl-4-n-propyl-dibenz[cd,f]indole produces 1281 rotations in the above Ungerstedt test at 5 mg/kg p.o., where bromocriptine produces 1600 rotations at 20 mg/kg p.o.

It is therefore indicated that the preferred compound of the invention may be administered at similar or lower dosages than conventionally employed for bromocriptine in the anti-parkinson utility.

In a 1st group of compounds $R_2$ is H.

In a 2nd group of compounds $R_2$ is alkyl.

In a 3rd group of compounds $R_2$ is cycloalkyl.

In a 4th group of compounds $R_2$ is cycloalkylalkyl.

What we claim is:

1. A compound of formula I in the (4S,5aR) isomer form or in racemate form

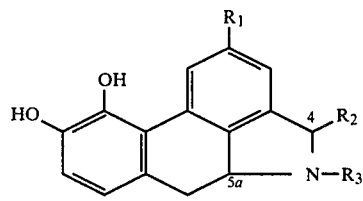

wherein
$R_1$ is $(C_{1-4})$alkyl,
$R_2$ is hydrogen, $(C_{1-10})$alkyl, $(C_{3-7})$cycloalkyl or $(C_{3-7})$cycloalkyl-$(C_{1-4})$alkyl, and
$R_3$ is $(C_{1-5})$alkyl,
or a physiologically hydrolysable and pharmaceutically acceptable ester thereof,
or a pharmaceutically acceptable acid addition salt of the compound or ester.

2. A compound of claim 1 wherein $R_2$ is $(C_{1-4})$alkyl and $R_3$ is $(C_{1-3})$alkyl, as a racemate or as the (4S,5aR) optical isomer, or a pharmaceutically acceptable acid addition salt of the racemate or isomer.

3. A compound of claim 1 which is (4S,5aR)-5-ethyl-4,5,5a,6-tetrahydro-9,10-dihydroxy-2-methyl-4-n-propyl-dibenz-[cd,f]indole, or a pharmaceutically acceptable acid addition salt thereof.

4. A compound of claim 1 which is (4S,5aR)-4,5,5a,6-tetrahydro-9,10-dihydroxy-2-methyl,4,5-di-n-propyl-dibenz[cd,f]indole, or a pharmaceutically acceptable acid addition salt thereof.

5. A method of treating a subject suffering from Morbus Parkinson which comprises administering an anti Morbus Parkinson amount of a compound of claim 1 or a pharmaceutically acceptable acid addition salt thereof to a subject in need of such treatment.

6. A pharmaceutical composition useful in the treatment of Morbus Parkinson comprising an anti-Parkinson effective amount of a compound according to claim 1 or a pharmaceutically acceptable acid addition salt of the compound in association with a pharmaceutical carrier or diluent.

7. The compound according to claim 1 which is (-)-(4S,5aR)-5-ethyl-4,5,5a,6-tetrahydro-9,10-dihydroxy-2-methyl-4-n-propyl-dibenz[cd,f]indole or a pharmaceutically acceptable acid addition salt thereof.

8. The compound according to claim 1 which is (-)-(4S,5aR)-4,5,5a,6-tetrahydro-9,10-dihydroxy-2-methyl-4,5-di-n-propyl-dibenz[cd,f]indole or a pharmaceutically acceptable acid addition salt therof.

* * * * *